United States Patent [19]

Crutzen et al.

[11] Patent Number: 4,530,241

[45] Date of Patent: Jul. 23, 1985

[54] METHOD OF MONITORING THE IDENTITY AND INTEGRITY OF AN OBJECT PARTICULARLY A CLOSED CONTAINER

[75] Inventors: Serge Crutzen, Orino; Gian Aldo Franzetti, Besozzo; Gian Piero Battagin, Angera, all of Italy

[73] Assignee: European Atomic Energy Community (Euratom), Luxembourg

[21] Appl. No.: 138,349

[22] Filed: Apr. 8, 1980

[30] Foreign Application Priority Data

Apr. 24, 1979 [GB] United Kingdom ............... 7914205

[51] Int. Cl.³ .................................... G01N 29/00
[52] U.S. Cl. .................................... 73/602
[58] Field of Search ............... 73/602, 594, 600, 627; 176/19 LD; 250/506, 507

[56] References Cited

U.S. PATENT DOCUMENTS

| | | |
|---|---|---|
| 3,641,811 | 2/1972 | Gnaedinger et al. ............... 73/594 |
| 4,126,514 | 11/1978 | Wonn . |
| 4,167,121 | 9/1979 | Mauch ............... 73/640 |
| 4,197,104 | 4/1980 | Krystyniak . |

FOREIGN PATENT DOCUMENTS

| | | |
|---|---|---|
| 2106013 | 4/1972 | France . |
| 2126794 | 10/1972 | France . |
| 2311300 | 12/1976 | France . |
| 520028 | 4/1972 | Switzerland . |
| 1241287 | 4/1971 | United Kingdom . |

OTHER PUBLICATIONS

Crutzen, S. J., et al., "Application of Tamper-Resistant Identification and Sealing Techniques for Safeguards", pp. 305-338.

Primary Examiner—Anthony V. Ciarlante
Attorney, Agent, or Firm—Stevens, Davis, Miller & Mosher

[57] ABSTRACT

Material such as fissile material (2) requiring to be safeguarded is stored inside a container (1) which is subsequently sealed, for example by a closure comprising a cover (3) and sealing element (30). The whole structure of the container (1) is ultrasonically scanned initially using piezo electric transducers (T1, T2) to obtain an output from which is derived a distinctive identity for the container (1), determined by the particular characteristics of the internal structure of at least a portion of the container, and also a reference signal indicative of the whole container structure when its integrity is intact. Subsequent ultrasonic scanning of the whole container structure, for example intermittently, produces a monitor signal which if different to the reference signal indicates the occurrence of a breach in the container's integrity. The distinctive identity for the container (1) may be derived from a distinctive internal structure of the cover (3) which preferably contains a material matrix, e.g. aluminium, having inclusions of, for example, tungsten, embedded therein in a random configuration.

6 Claims, 4 Drawing Figures

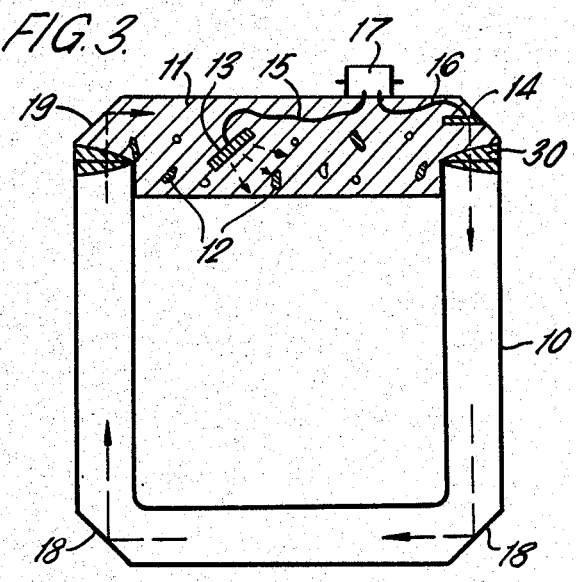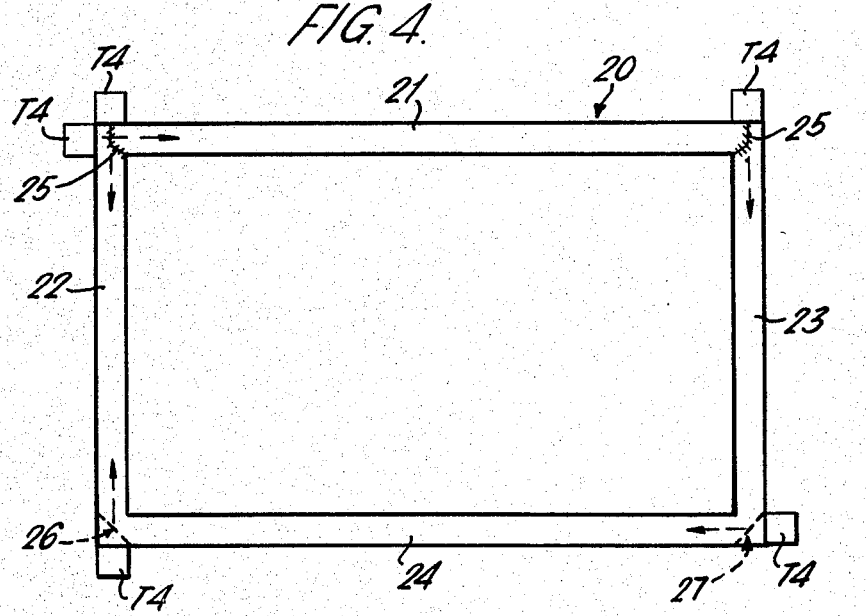

METHOD OF MONITORING THE IDENTITY AND INTEGRITY OF AN OBJECT PARTICULARLY A CLOSED CONTAINER

The present invention relates to a method for monitoring the identity and integrity of an object, particularly, but not exclusively, a closed container for containing members requiring secure storage, such as fissile material.

Under the provisions of the Treaty of Non Proliferation, all fissile material must be continually and carefully controlled, i.e. monitored, from the manufacture of the nuclear fuel elements, to their reprocessing after use, in order to prevent the fissile material or any part thereof being tampered with or substituted by unauthorised personnel. The control of the material may be visual, using TV cameras for example, or may be ensured by the storage of the fissile material in containers which by their solidity and robustness are able to preserve their integrity, i.e. discourage tampering. The containers are generally sealed and sometimes monitoring of the integrity of the seal may be sufficient to produce adequate control of the integrity of the container itself.

In practice, the containers are frequently stored in a location which is both protected and armoured. Sometimes, the container to be monitored is stored in a site which is poorly illuminated, or is physically inaccessible. In addition, if the container is used for storing fissile material, the presence of radiation makes difficult if not impossible the use of delicate monitoring devices.

Particularly where the container is used to store material having a high strategic value such as plutonium, it is extremely important to be able to provide adequate control and monitoring of the container integrity.

One prior proposal for identifying a container in which fissile material is stored, for example a cylindrical container containing a bundle of nuclear fuel elements, involves the incorporation on the container of an identifier in the cover of the container; the identifier having a distinctive internal structure which when ultrasonically scanned provides the distinctive identity for the container. Such an identifier is described in our earlier British Patent Specification No. 1241287. Thus if the cover has been tampered with, subsequent scanning of the identifier will reveal a difference in the output produced, and thus the existence of the breach in the integrity of the identifier. However, if the body of the container has been tampered with in any way, for example has been cut and subsequently welded, then scanning the cover incorporating the identifer will not reveal the unauthorised opening of the container. The present invention is concerned with a solution to this problem.

According to the present invention, there is provided a method of monitoring the identity and integrity of an object, including the steps of initially scanning the object ultrasonically by transmitting ultrasonic signals throughout the structure thereof to derive from the output produced a distinctive identity for the object determined by the structure of at least a predetermined portion of the object, and also to derive from said output a reference signal indicative of the whole structure of the object when its integrity is intact; subsequently scanning the whole object ultrasonically to obtain a monitor signal indicative of the current structure thereof; and comparing the monitor signal with said reference signal to discover the existence of any difference therebetween indicating that the integrity of the structure has been breached.

Preferably, the object to be monitored is a container, the initial and subsequent ultrasonic scanning operations both involving the transmission of ultrasonic signals along each of the walls of the container.

The invention is also concerned with the provision of a closed container for containing material to be safeguarded, for example fissile material, including means for transmitting ultrasonic signals along each of the walls of the container, whereby, in use, said transmitter means can initially be energized to scan ultrasonically the walls of the container to provide a distinctive identity for the container determined by the structure of at least a predetermined portion thereof and a reference signal indicative of the structure of the whole container when its integrity is intact, and subsequently be energized to provide a monitor signal indicative of the current state of integrity of the whole container which when compared to said reference signal produces an indication as to the occurrence of a breach in the integrity of the container.

Preferably, one of the container walls incorporates a closure which includes an identifying portion having a distinctive internal structure which when ultrasonically scanned can provide said distinctive identity for the container.

The term "closure" is used herein to indicate the cover for a container and also, if provided, any sealing element or other means, e.g. welding, by which the cover is, in use, fitted to the container walls.

Reference is now made to the accompanying drawings, which illustrate by way of example various embodiments of the invention, and of which:

FIG. 3 shows a diagrammatic section of a container according to a further embodiment of the invention; and FIG. 4 shows a diagrammatic section of a container such as a strong-room according to yet a further embodiment of the invention.

Figure 1:
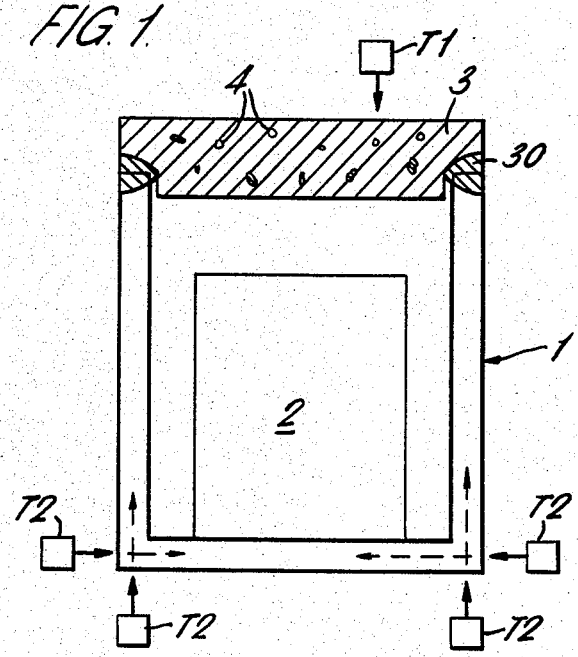
FIG. 1 shows a diagrammatic section of a container according to one embodiment of the invention.

In FIG. 1, a container 1 for containing fissile elements or other material to be safeguarded, generally indicated by reference numeral 2, is provided with a closure, constituted by a cover 3 and a sealing element 30 which may be a weld and which surrounds the periphery of the cover 3. The cover 3 is either constituted by or incorporates an identifier such as is described in our British Patent Specification No. 1241287, having a matrix of, for example, aluminium, in which are embedded in a random configuration a plurality of inclusions, for example tungsten particles. The distinctive internal structure of the cover 3 is therefore able to provide a distinctive identity for the container when it is scanned by a piezo electric transducer T1 applied to the cover.

The integrity of the container 1 is monitored by the application of further piezo electric transducers T2 which are applied to the outside of the container so as to be able to transmit ultrasonic signals along each of the walls of the container. Thus once a reference has been established by ultrasonic scanning when the container is known to be intact, a subsequent scan of the container using the transducers T2 and producing a result which differs from the reference will reveal the occurrence of an unauthorised breach of the integrity of the container.

Figure 2:
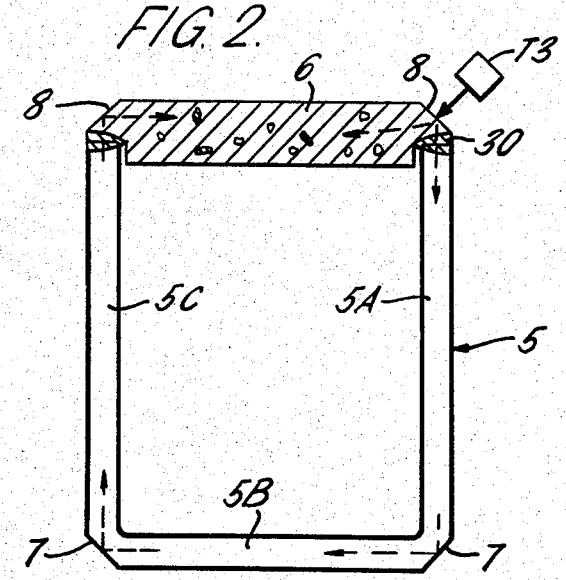
FIG. 2 shows a diagrammatic section of a modified version of the container of FIG. 1.

A modified version of this container is shown in FIG. 2, where the container 5 is closed by a cover 6 which, like cover 3 of FIG. 1, is secured on the container by a sealing weld 30, and includes or incorporates an identifier which when ultrasonically scanned can provide a distinctive identity for the container. The corners 7 of the container 5 and the corners 8 of the cover 6 are all chamfered at 45°. A twin-crystal piezo electric transducer T3 is applied to one of the corners 8 of the cover 6, so that it emits ultrasonic signals in two directions, namely across the cover 8 in order to derive the distinctive identity of the container as in the previous embodiment, and also through sealing weld 30 and the wall 5A of the container 5, as illustrated by the arrows in FIG. 2. When the signal transmitted through wall 5A encounters the chamfered corner 7, the chamfered corner acts like a mirror to reflect the signal at 90° across the wall 5B, until it encounters the second chamfered corner 7, whereat it is reflected a second time along the wall 5C. When the signal leaves wall 5C and enters the cover 6 via the sealing weld 30, it encounters the chamfered corner 8 shown at the left hand side in FIG. 2, which in similar fashion acts as a mirror to reflect the ultrasonic signal from left to right across the cover until it is picked up by the transducer T3 to produce the appropriate ultrasonic output. In other words, the integrity of the container walls and the composite closure (i.e. the cover 3 and the sealing weld 30), and the distinctive identity of the container can be established by the transducer T3 on its own.

The transducers T1, T2 and T3 shown in FIGS. 1 and 2 may be mounted on the container either during its construction, or when the container is filled with material to be stored therein, and provided with suitable means for subsequent electrical connection to ultrasonic scanning apparatus, in order that the scanning of the container can be controlled from a remote location. This is clearly useful where the container is to be located in a physically inaccessible site, or is in an area subjected to radiation hazard.

FIG. 3 shows an embodiment of the invention which provides a container which is suitable for use in extremely inaccessible locations, because the transducers emitting the ultrasonic signals are located inside the cover, rather than on the outside of the container. The container 10 is provided with a cover 11, which like the cover 3 of FIG. 1 is secured to the container by a sealing weld 30, but in this embodiment, the cover 11 is constituted by an identifier having a matrix of aluminium in which are embedded in random configuration a plurality of bronze or tungsten particles 12. Also acting as inclusions in the matrix material are two piezo electric transducers 13 and 14, respectively electrically connected by leads 15 and 16 to a common conductor 17 which is exposed on the outside of the cover 11. The output of the transducer 13, when energized, is dependent on the particular configuration of the inclusions in the matrix material of the cover, and therefore is used in the derivation of the distinctive identity of the container. The other transducer 14 is mounted at the side of the cover, so that when energised it transmits an ultrasonic signal through the adjacent wall of the container via the sealing weld 30, the signal being successively reflected through all the walls of the container 10 by chamfered corners 18 on the container, as in the embodiment of FIG. 2, and subsequently by a chamfered corner 19 on the cover, before being picked up once again by the transducer 14 to provide an indication of the integrity of the container itself.

It should be noted that if the transducer 14 is a twin-crystal pizeo electric transducer, it would be possible to omit the transducer 13, leaving the twin-crystal transducer to transmit the ultrasonic signals across the cover and through the walls of the container necessary to provide both the identity of the container and the indication of its integrity.

FIG. 4 shows yet a further embodiment of the invention, in which the container takes the form of a metal strong-room 20, of which the walls are welded together. In FIG. 4, only the top wall 21, side walls 22 and 23 and bottom wall 24 are visible. Typically, each wall is formed from welded plates, and is welded to the adjacent walls. When ultrasonic signals are transmitted through each wall of the strong-room by means of transducers T4 suitably placed at the corners of the strong-room, the output produced can be used to derive an indication of the integrity of the strong-room, and also of the distinctive identity of the strong-room because the output will be affected by distinctive features of the strong-room construction such as the location and shape of welds in the walls, for example welds 25 between the top wall 21 and side walls 22, 23, the entry door into the strong-room, and a possible observation window in the walls, neither of which is visible.

As before, subsequent ultrasonic scanning of the walls can provide an indication as to the occurrence of an unauthorized breach of the strong-room.

As in previous embodiments shown in FIGS. 2 and 3, the corners of the strong-room, such as corners 26 and 27 respectively between the walls 22, 24 and 23, 24, may be chamfered at 45°, producing corresponding reflection of the ultrasonic signals in the wall, and thereby reducing the number of transducers required for the transmission of ultrasonic signals throughout the strong-room structure.

The integrity checks on the containers shown in the drawings are described above as using the ultrasonic transmission technique. As an alternative, the ultrasonic echo technique may be used, since if an altered zone is present in a wall, whether due, for example to re-welding or re-soldering after cutting, or not, the variation in the structure of this zone will produce a back echo or back scattering of the ultrasonic waves towards the ultrasonic emitter/transducer and thus provide an indication that a change in structure has occurred and thereby demonstrate tampering.

We claim:

1. A closed container for containing material to be safeguarded comprising: a plurality of walls defining said closed container, at least one of said walls being a closure member, having a distinctive internal structure for identifying said container, said distinctive internal structure comprising a material matrix having embedded therein inclusions disposed in a random configuration, a transmitting means for transmitting ultrasonic signals through said distinctive internal structure to provide a signal representative of the identity of said container and for transmitting ultrasonic signals through all walls of said container to provide a signal representative of the entire wall structure of said closed container.

2. A closed container as claimed in claim 1, in which one of said inclusions is constituted by a transducer comprising at least a part of said transmitting means and being capable, when energized, of transmitting ultrasonic signals through said distinctive internal structure to provide said identity signal of the container.

3. A closed container as claimed in claim 1, in which one of said inclusions is constituted by a transducer comprising at least a part of said transmitting means and disposed so as to be able, when energized, to transmit ultrasonic signals along at least one of the container walls other than that incorporating said closure member.

4. A closed container as claimed in claim 1, in which one of said inclusions is constituted by a transducer comprising at least a part of said transmitting means and being capable, when energized, of transmitting ultrasonic signals through said distinctive internal structure to provide said identity signal, and a second of said inclusions is constituted by a second transducer comprising at least a part of said transmitting means and disposed so as to be able, when energized, to transmit ultrasonic signals along at least one of the container walls other than that incorporating said closure member.

5. A closed container for containing material to be safeguarded comprising: a plurality of walls defining said closed container, the corners defined by adjacent container walls being chamfered at an angle of substantially 45°, means for transmitting ultrasonic signals along each of said walls and comprising a single transducer containing twin piezoelectric crystals and disposed so as to transmit ultrasonic signals in two directions along the walls of said container, said signals being reflected from one wall to the next adjacent wall by said chamfered corners, said transmitting means being energizable to ultrasonically scan the walls of said container to generate a distinctive identity signal for said container as determined by the structure of a predetermined portion thereof and a reference signal indicative of the structure of the entire container when its integrity is intact.

6. A closed container for containing material to be safeguarded comprising: a plurality of walls defining said closed container as a box-like structure at least one of said walls being a closure member, at least one of said walls having a distinctive internal structure for identifying said container, a transmitting means for transmitting ultrasonic signals through said distinctive internal structure to provide a signal representative of the identity of said container and for transmitting ultrasonic signals through all walls of said container to provide a signal representative of the entire wall structure of said closed container, said transmitting means comprising one or more transducers arranged to transmit ultrasonic signals along each wall of the container, at least one of the corners of said box-like structure being formed by the junction of two adjacent walls being chamfered at 45° thereby to reflect ultrasonic signals from one of said adjacent walls.

* * * * *